(12) United States Patent
Lee et al.

(10) Patent No.: US 10,263,580 B2
(45) Date of Patent: Apr. 16, 2019

(54) POWER SUPPLYING APPARATUS FOR NEURAL ACTIVITY RECORDER REDUCING COMMON-MODE SIGNAL APPLIED TO ELECTRODES CONNECTED TO THE NEURAL ACTIVITY RECORDER

(71) Applicant: DAEGU GYEONGBUK INSTITUTE OF SCIENCE AND TECHNOLOGY, Daegu (KR)

(72) Inventors: Jung Hyup Lee, Daegu (KR); Sehwan Lee, Gyeongsangbuk-do (KR); Minkyu Je, Daejeon (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 0 days.

(21) Appl. No.: 15/887,172

(22) Filed: Feb. 2, 2018

(65) Prior Publication Data
US 2018/0219518 A1   Aug. 2, 2018

(30) Foreign Application Priority Data
Feb. 2, 2017 (KR) .................. 10-2017-0015060

(51) Int. Cl.
| | |
|---|---|
| H03F 3/345 | (2006.01) |
| H03F 3/45 | (2006.01) |
| H02J 1/10 | (2006.01) |
| A61B 5/04 | (2006.01) |
| A61B 5/00 | (2006.01) |

(Continued)

(52) U.S. Cl.
CPC ......... *H03F 3/4565* (2013.01); *A61B 5/0006* (2013.01); *A61B 5/04001* (2013.01); *H02J 1/10* (2013.01); *H03F 3/345* (2013.01); *H03F 3/393* (2013.01); *H03F 3/45183* (2013.01); *H03F 3/45224* (2013.01); *H03F 3/45237* (2013.01); *H03F 3/45475* (2013.01); *H03F 3/72* (2013.01); *H03F 2200/261* (2013.01); *H03F 2203/45136* (2013.01); *H03F 2203/45138* (2013.01); *H03F 2203/45424* (2013.01); *H03F 2203/45524* (2013.01); *H03F 2203/45526* (2013.01)

(58) Field of Classification Search
USPC ................................................ 330/252–261
See application file for complete search history.

(56) References Cited

U.S. PATENT DOCUMENTS

| | | | | |
|---|---|---|---|---|
| 7,941,210 | B2 * | 5/2011 | Matthiessen | ......... A61B 5/0536 324/600 |
| 2007/0010758 | A1 | 1/2007 | Matthiessen et al. | |

OTHER PUBLICATIONS

Abdelhalim et al., "64-Channel UWB Wireless Neural Vector Analyzer SOC With a Closed-Loop Phase Synchrony-Triggered Neurostimulator," IFEE Journal of Solid-State Circuits, vol. 47, No. 10, Oct. 2013, 2494-2510.

(Continued)

*Primary Examiner* — Hieu P Nguyen
(74) *Attorney, Agent, or Firm* — Hoffman Warnick LLC

(57) ABSTRACT

Disclosed is a differential voltage supplying apparatus configured to supply, to a neural activity recorder, an input signal generated by combining, with a direct current (DC) power supply, a common-mode signal determined from a voltage applied to a detection electrode and a reference electrode connected to the neural activity recorder, and improve a common-mode rejection ratio of the neural activity recorder and generate a DC power supply.

4 Claims, 16 Drawing Sheets

(51) Int. Cl.
*H03F 3/72* (2006.01)
*H03F 3/393* (2006.01)

(56) References Cited

OTHER PUBLICATIONS

Jochum et al., "Integrated circuit amplifiers for multi-electrode intracortical recording," Journal of Neural Engineering, 6(2009) 012001, 27 pages.
Lee et al., "A 110 dB-CMRR 100dB-PSRR Multi-Channel Neural Recording Amplifier System Using Differentially Regulated Rejection Ratio Enhancement in 0.18 μm CMOS," 14 pages, undated.

* cited by examiner

FIG. 8

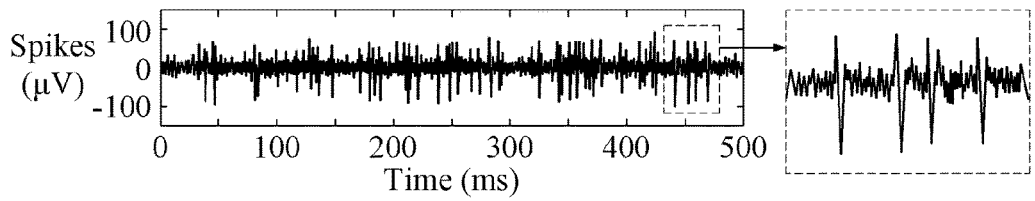

| Parameter | ISSCC11 [2] | ISSCC13 [3] | JSSC14 [4] | JSSC16 [1] | This work |
|---|---|---|---|---|---|
| Technology [nm CMOS] | 65 | 180 | 180 | 65 | 180 |
| Supply voltage [V] | 0.5 | 0.45 | 1.8 | 1.0 | 1.5 |
| Power per channel [μW] | 5.04 | 0.73 | 7.02 | 3.28 | $3.23^1$ $(0.69)^2$ |
| Mid-band gain [dB] | N.A. | 52 | 30-72 | 52.1 | 39.8 |
| Operating Bandwidth [Hz] | 300-10k | 1-10k | 300-6k | 1-8.2k | 10-10k |
| Channel area [mm$^2$] | 0.013 | N.A. | 0.088 | 0.042 | 0.075 |
| Input referred noise [μV$_{rms}$] | 4.9 | 3.2 | 3.2 | 4.13 | 3 |
| %THD (at input amplitude) | N.A. | 0.53 (0.5mVp) | 1 (18mVp) | 1 (0.7mVp) | 0.37 (2mVp) |
| NEF/PEF | 5.99/17.96 | 1.57/1.12 | 3.08/17.13 | 3.19/10.2 | $1.69/4.28^1$ $(1.3/1.01)^2$ |
| CMRR [dB] | 75 | 73 @1kHz | 60 | >80 @1kHz | >110 @1kHz |
| TCMRR [dB] | N.A. | N.A. | N.A. | >59.6 @1kHz, $Z_0$=100kΩ | >80 @1kHz, $Z_0$=100kΩ |
| PSRR [dB] | 64 | 80 @1kHz | 76 | 78 @1kHz | 101 @1kHz |

$^1$w/ DR$^3$E
$^2$w/o DR$^3$E

POWER SUPPLYING APPARATUS FOR NEURAL ACTIVITY RECORDER REDUCING COMMON-MODE SIGNAL APPLIED TO ELECTRODES CONNECTED TO THE NEURAL ACTIVITY RECORDER

CROSS-REFERENCE TO RELATED APPLICATION(S)

This application claims the priority benefit of Korean Patent Application No. 10-2017-0015060 filed on Feb. 2, 2017, in the Korean Intellectual Property Office, the disclosure of which is incorporated herein by reference for all purposes.

BACKGROUND

1. Field

One or more example embodiments relate to a power supplying apparatus used for a neural activity recorder, and more particularly, to a power supplying apparatus with an improved common-mode rejection ratio.

2. Description of Related Art

A neural activity recorder may be connected to a detection electrode provided for each of channels of the neural activity recorder, a reference electrode configured to provide a reference voltage to measure a voltage of the detection electrode, and a ground electrode configured to emit noise of the neural activity recorder. The detection electrode and the reference electrode may be connected to a low-noise amplifier (LNA) of the neural activity recorder, and the ground electrode may be connected to a ground of the neural activity recorder.

The neural activity recorder may collect neural signals such as an action potential and a local field potential using a potential difference between the detection electrode and the reference electrode. Herein, a plurality of detection electrodes whose number is equal to the number of the channels of the neural activity recorder may be provided, and a single ground electrode and a single reference electrode may be provided. The neural activity recorder may include a same number of LNAs as the number of the channels. A positive input terminal of each of the LNAs may be connected to each of the detection electrodes. The reference electrode may be connected to negative input terminals of all the LNAs.

Thus, an input impedance mismatch indicating that an impedance of a positive input terminal and an impedance of a negative input terminal of each of the LNAs differ from each other may occur. The impedance of the positive input terminal and the impedance of the negative input terminal may differ from each other, and thus a common-mode rejection ratio of the neural activity recorder may be reduced.

SUMMARY

An aspect provides a power supplying apparatus that may improve a common-mode rejection ratio of a neural activity recorder.

The common-mode rejection ratio of the neural activity recorder connected to the power supplying apparatus may be improved by at least 40 decibels (dB) compared to a common-mode rejection ratio of an existing neural activity recorder.

According to an aspect, there is provided a differential voltage supplying apparatus including a differential voltage generator configured to generate a first input signal and a second input signal from a power supply, and a common-mode signal combiner configured to combine a common-mode signal with each of the first input signal and the second input signal such that the first input signal and the second input signal that are combined with the common-mode signal are supplied to a neural activity recorder. Herein, a difference between the first input signal and the second input signal may be determined based on a preset potential difference. The common-mode signal may be determined based on a voltage applied to an electrode attached to a body of a user to allow the neural activity recorder to measure a neural activity of the user.

The common-mode signal combiner may determine the common-mode signal using a common-mode signal electrode configured to measure a voltage applied to an electrode of the neural activity recorder.

The differential voltage generator may generate the first input signal and the second input signal separated from the power supply and a ground electrode.

The common-mode signal combiner may combine the common-mode signal with each of the first input signal and the second input signal to compensate for an influence of an impedance of a positive input terminal of a low-noise amplifier (LNA) included in the neural activity recorder and an impedance of a negative input terminal of the LNA, on a common-mode rejection ratio of the LNA.

According to example embodiments described herein, a common-mode rejection ratio of a neural activity recorder may be improved.

In addition, the common-mode rejection ratio of the neural activity recorder connected to a power supplying apparatus may be improved by at least 40 dB compared to a common-mode rejection ratio of an existing neural activity recorder.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the present disclosure will become apparent and more readily appreciated from the following description of example embodiments, taken in conjunction with the accompanying drawings of which:

FIG. 8 is a diagram illustrating an example transfer function and an accuracy of an FCDR according to an example embodiment.

DETAILED DESCRIPTION

Figure 1:
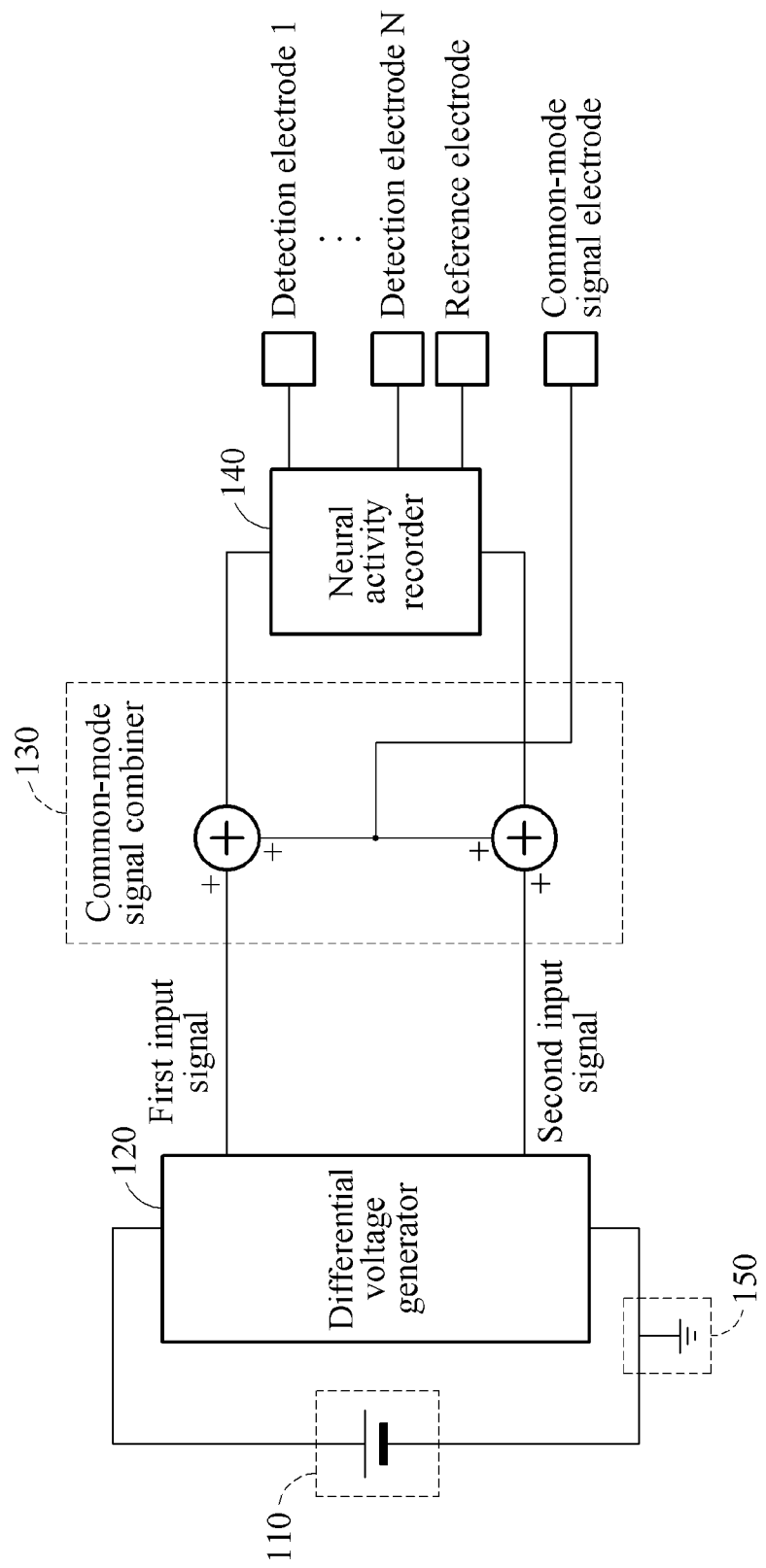
FIG. 1 is a diagram illustrating a structure of a neural activity recorder connected to a differential voltage generator and a common-mode signal combiner according to an example embodiment.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Terms such as first, second, A, B, (a), (b), and the like may be used herein to describe components. Each of these terminologies is not used to define an essence, order, or sequence of a corresponding component but used merely to distinguish the corresponding component from other component(s). For example, a first component may be referred to as a second component, and similarly the second component may also be referred to as the first component.

It should be noted that if it is described in the specification that one component is "connected," "coupled," or "joined" to another component, a third component may be "connected," "coupled," and "joined" between the first and second components, although the first component may be directly connected, coupled or joined to the second component. In addition, it should be noted that if it is described in the specification that one component is "directly connected" or "directly joined" to another component, a third component may not be present therebetween. Likewise, expressions, for example, "between" and "immediately between" and "adjacent to" and "immediately adjacent to" may also be construed as described in the foregoing.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, operations, elements, and/or components, but do not preclude the presence or addition of one or more other features, integers, operations, elements, components, and/or groups thereof.

Unless otherwise defined, all terms, including technical and scientific terms, used herein have the same meaning as commonly understood by one of ordinary skill in the art to which this disclosure pertains based on an understanding of the present disclosure. Terms, such as those defined in commonly used dictionaries, are to be interpreted as having a meaning that is consistent with their meaning in the context of the relevant art and the present disclosure, and are not to be interpreted in an idealized or overly formal sense unless expressly so defined herein.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings.

FIG. 1 is a diagram illustrating a structure of a neural activity recorder 140 connected to a differential voltage generator 120 and a common-mode signal combiner 130 according to an example embodiment.

Referring to FIG. 1, the differential voltage generator 120 may generate a first input signal and a second input signal from a power supply 110. Herein, a difference between the first input signal and the second input signal may be determined based on a preset potential difference. That is, a difference between a voltage of the first input signal and a voltage of the second input signal may be determined to maintain the preset potential difference.

The first input signal and the second input signal that are generated by the differential voltage generator 120 may be used as a power supply for the neural activity recorder 140. That is, the differential voltage generator 120 may generate such an independent power supply that is separated from the power supply 110 and a ground. The neural activity recorder 140 may collect a plurality of neural activities through channels respectively corresponding to the neural activities. The neural activity recorder 140 may be connected to a detection electrode provided for each of the channels, and to a reference electrode configured to provide a reference voltage to measure a voltage of the detection electrode. The detection electrode and the reference electrode may be attached to different portions of a body of a user.

The neural activity recorder 140 may include a low-noise amplifier (LNA) provided for each of the channels. A positive input terminal of the LNA may be connected to a corresponding detection electrode, and a negative input terminal of the LNA may be connected to the reference electrode. The LNA may receive power from the first input signal and the second input signal.

The common-mode signal combiner 130 may combine a common-mode signal with each of the first input signal and the second input signal and supply, to the neural activity recorder 140, the first input signal and the second input signal that are combined with the common-mode signal. The common-mode signal may be determined based on a voltage applied to an electrode attached to the body of the user, for example, the detection electrode and the reference electrode, to allow the neural activity recorder 140 to measure a neural activity of the user. As illustrated in FIG. 1, the common-mode signal combiner 130 may be connected to a common-mode signal electrode configured to measure the common-mode signal. The common-mode signal combiner 130 may determine the common-mode signal to be combined with each of the first input signal and the second input signal, based on a voltage of the connected common-mode signal electrode.

As illustrated in FIG. 1, a direct current (DC) power supply generated from the common-mode signal added to a ground electrode 150 of the power supply may be input to the neural activity recorder 140. Thus, a change in voltage on an input side of the neural activity recorder 140 may be the same as a change in common-mode signal measured from an input of the LNA. Therefore, a magnitude of a common-mode signal indicated at the input of the LNA may be negligible, and thus a common-mode rejection ratio of the neural activity recorder 140 may be improved.

Figure 2:
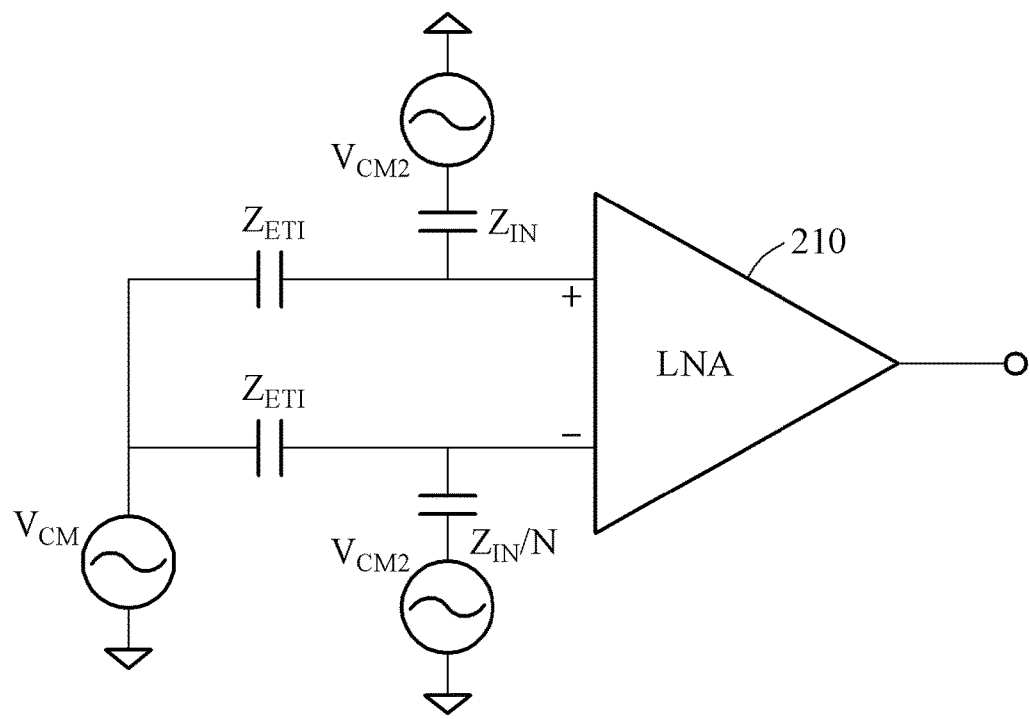
FIG. 2 is a diagram illustrating an example of how a common-mode rejection ratio of a neural activity recorder is improved by receiving a first input signal and a second input signal that are combined with a common-mode signal according to an example embodiment.

FIG. 2 is a diagram illustrating an example of how a common-mode rejection ratio of a neural activity recorder is improved by receiving a first input signal and a second input signal that are combined with a common-mode signal according to an example embodiment. FIG. 2 also illustrates an equivalent circuit for an LNA 210 provided for each of channels of a neural activity recorder.

Referring to FIG. 2, a detection electrode may be connected to a positive input terminal of the LNA 210, and a reference electrode may be connected to a negative input terminal of the LNA 210. When the neural activity recorder collects neural activities through corresponding channels, the reference electrode may be connected to negative input terminals of all LNAs included in the neural activity recorder. The detection electrode and the reference electrode may be attached to different portions of a body of a user. The neural activity recorder may detect a neural activity of the user, based on a potential difference between the detection electrode and the reference electrode that is amplified through the LNA 210.

Referring to FIG. 2, $Z_{IN}$ indicates an input impedance of the LNA 210. Because all the negative input terminals of the LNAs of the neural activity recorder are connected to the reference electrode, an input impedance of a negative input terminal with respect to N channels may be $Z_{IN}/N$. In addition, an input impedance of the positive input terminal of the LNA 210 is $Z_{IN}$ and an input impedance of the negative input terminal of the LNA 210 is $Z_{IN}/N$, and thus an impedance of the positive input terminal and an impedance of the negative input terminal may differ from each other. As the number of the channels, for example, N, increases, such a difference between the impedances may also increase.

Referring to FIG. 2, $Z_{ETI}$ indicates an equivalent impedance of the detection electrode or the reference electrode, and a tissue. $V_{CM}$ indicates a voltage of a common-mode signal measured at the detection electrode and the reference electrode, and $V_{CM2}$ indicates a voltage of a common-mode signal combined with each of a first input signal and a second input signal to be input to a power supply electrode of the neural activity recorder by a common-mode signal combiner.

Referring to the equivalent circuit illustrated in FIG. 2, a common-mode rejection ratio $CMRR_{sys}$ of the LNA 210 may be determined as represented by Equation 1 below.

$$CMRR_{sys} = \left(\frac{1}{1 - \frac{V_{CM2}}{V_{CM}}}\right)\left(\frac{1}{CMRR_{AMP}} + \left(\frac{N + 1 + 2\left(\frac{Z_{IN}}{Z_{ETI}}\right)}{2(N-1)}\right)^{-1}\right)^{-1} \quad \text{[Equation 1]}$$

In Equation 1, $CMRR_{AMP}$ denotes a common-mode rejection ratio CMRR of the LNA 210. Because the LNA 210 is not an ideal operational amplifier (OP-AMP), a value of $CMRR_{AMP}$ may be determined to be a finite value based on an internal element of the LNA 210. Referring to Equation 1, a common-mode rejection ratio of the LNA 210 may be improved by $$\left(\frac{1}{1 - \frac{V_{CM2}}{V_{CM}}}\right).$$

The common-mode signal measured through the common-mode signal electrode is combined with each of the first input signal and the second input signal. Thus, in theory, there is no difference between the voltage $V_{CM}$ of the common-mode signal measured through the common-mode signal electrode and the voltage $V_{CM2}$ of the common-mode signal combined with each of the first input signal and the second input signal. There may be no difference between the voltage $V_{CM}$ and the voltage $V_{CM2}$, and thus the common-mode rejection ratio $CMRR_{sys}$ may become infinite in theory.

However, when the common-mode signal is combined with each of the first input signal and the second input signal, there may be a slight difference between the voltage $V_{CM}$ of the common-mode signal measured through the common-mode signal electrode and the voltage $V_{CM2}$ of the common-mode signal combined with each of the first input signal and the second input signal. Despite such a difference between the voltage $V_{CM}$ and the voltage $V_{CM2}$, the common-mode rejection ratio $CMRR_{sys}$ may be improved by 40 decibels (dB) or more.

In conclusion, the common-mode signal combiner may combine, with a first input signal and a second input signal, a common-mode signal measured at a detection electrode or a reference electrode, and thus improve a common-mode rejection ratio of the neural activity recorder. Thus, an influence of a difference between an impedance of a positive input terminal of an LNA and an impedance of a negative input terminal of the LNA on the common-mode rejection ratio may be compensated for by the common-mode signal combiner, and thus, although the number of channels of the neural activity recorder increases, the common-mode rejection ratio of the neural activity recorder may be maintained at a certain value or greater.

In detail, referring back to Equation 1, when the number of channels is 1 (N=1) and there is no difference between the impedance of the positive input terminal of the LNA 210 and the impedance of the negative input terminal of the LNA 210, the common-mode rejection ratio $CMRR_{sys}$ of the LNA 210 may be $$\left(\frac{1}{1 - \frac{V_{CM2}}{V_{CM}}}\right)CMRR_{AMP}.$$

The common-mode rejection ratio $CMRR_{sys}$ may be represented as $$20\log\left(\frac{1}{1 - \frac{V_{CM2}}{V_{CM}}}\right) + 20\log(CMRR_{AMP})$$

on a log scale. That is, the common-mode rejection ratio $CMRR_{sys}$ of the LNA 210 may be limited by $CMRR_{AMP}$.

Thus, although a difference between the impedance of the positive input terminal of the LNA 210 and the impedance of the negative input terminal of the LNA 210 occurs as the number of channels, for example, N, increases, the common-mode rejection ratio $CMRR_{sys}$ may be maintained at $$20\log\left(\frac{1}{1-\frac{V_{CM2}}{V_{CM}}}\right)$$

or greater. The neural activity recorder may minimize the difference between the voltage $V_{CM}$ and the voltage $V_{CM2}$, the common-mode rejection ratio $CMRR_{sys}$ may be improved. For example, in a case in which an error between the voltage $V_{CM}$ and the voltage $V_{CM2}$ is less than 1%, $$0.99 < \frac{V_{CM2}}{V_{CM}} < 1.01,$$

and thus the common-mode rejection ratio $CMRR_{sys}$ may be improved by 40 dB or more.

Figure 3:
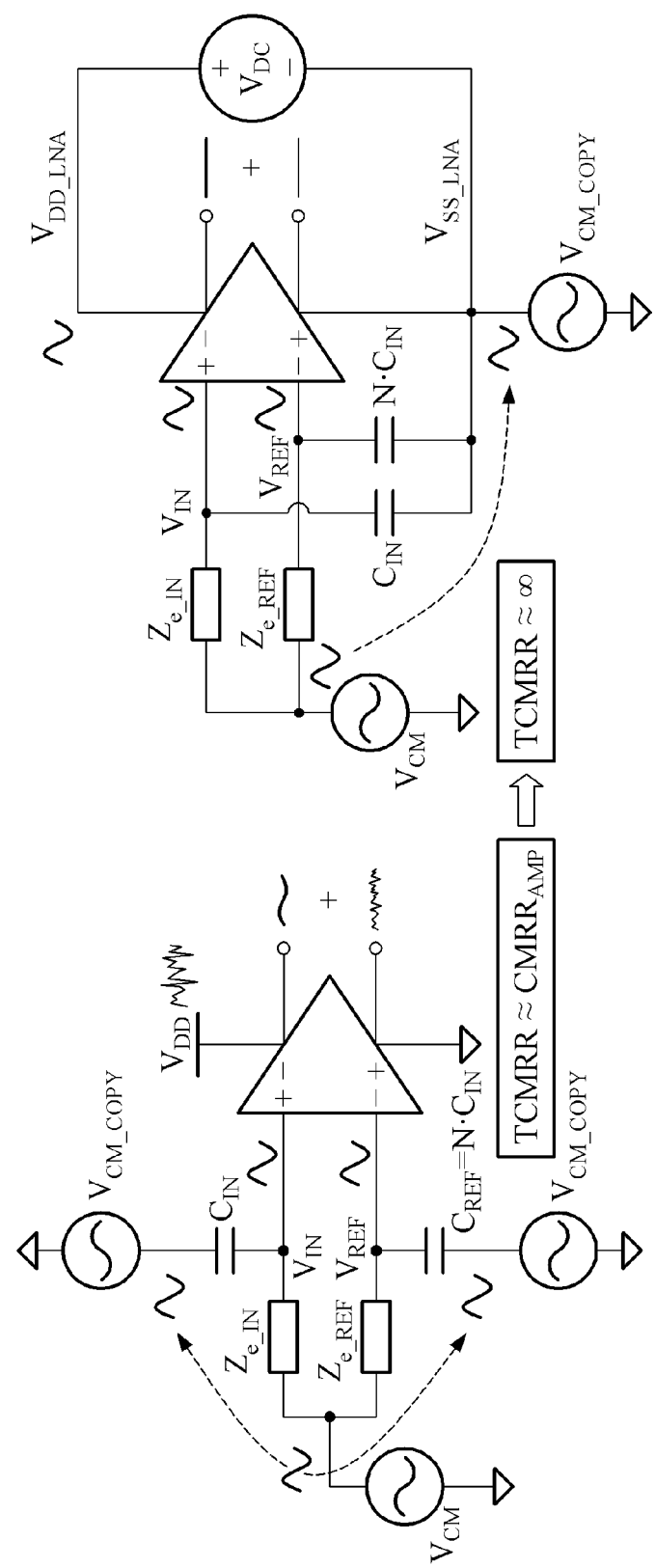
FIG. 3 is a diagram illustrating a structure of a neural activity recorder according to an example embodiment.

FIG. 3 is a diagram illustrating a structure of a neural activity recorder according to an example embodiment. The neural activity recorder described herein may be used to analyze neural activities of a human brain.

A multi-channel neural recording amplifier system according to an example embodiment employing a differentially regulated rejection ratio enhancement ($DR^3E$) scheme is illustrated in FIG. 3. The key idea of this method is to superimpose the system ground with the common-mode signal $V_{CM}$, so that potential division does not happen between $Z_e$ and $Z_{CIN}$ at the amplifier inputs. Secondly, a floating voltage $V_{DC}$, referenced from this ground is used as the amplifier supply.

As a result, common-mode disturbances may not affect the differential output even in the presence of input-impedance mismatches or when the CM rejection capability of the amplifier becomes limited. Thus, refer to FIG. 3, the TCMRR of the amplifier may theoretically be infinite, limited only by the accuracy of the common-mode superimposition. Furthermore, as the amplifier rails are isolated from the system rails, a high PSRR follows as a natural consequence.

Figure 4A:
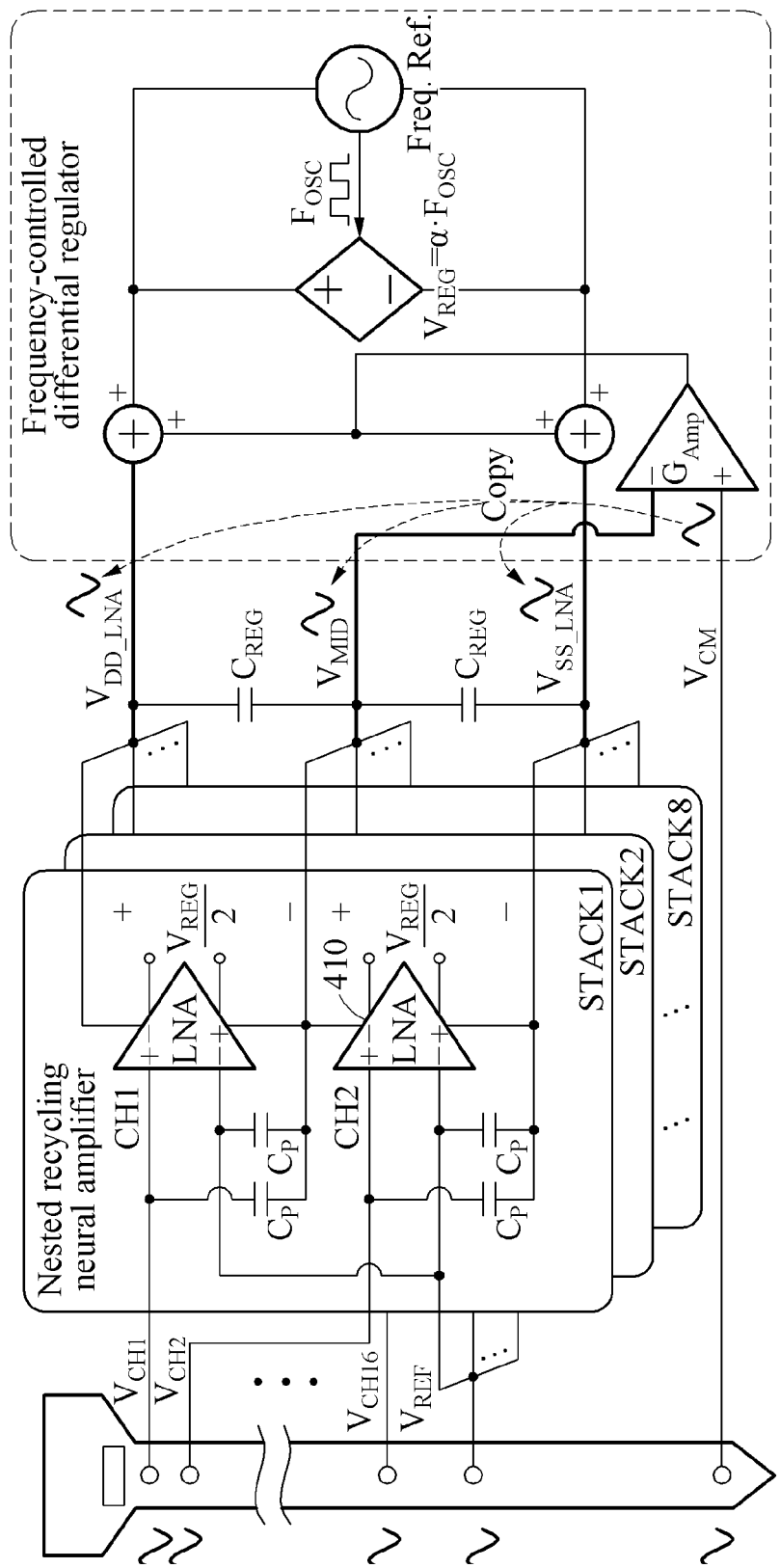
FIGS. 4A through 4C are diagrams illustrating an architecture and a low-noise amplifier (LNA) of a 16-channel neural recording amplifier system according to an example embodiment.
Figure 4B:
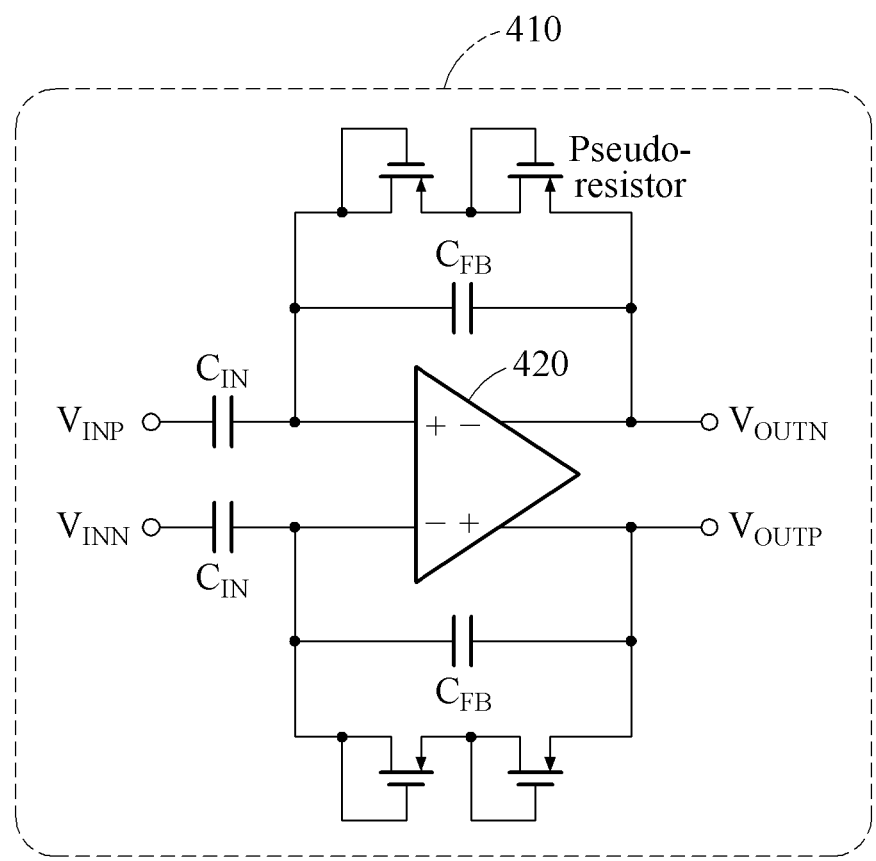
Figure 4C:
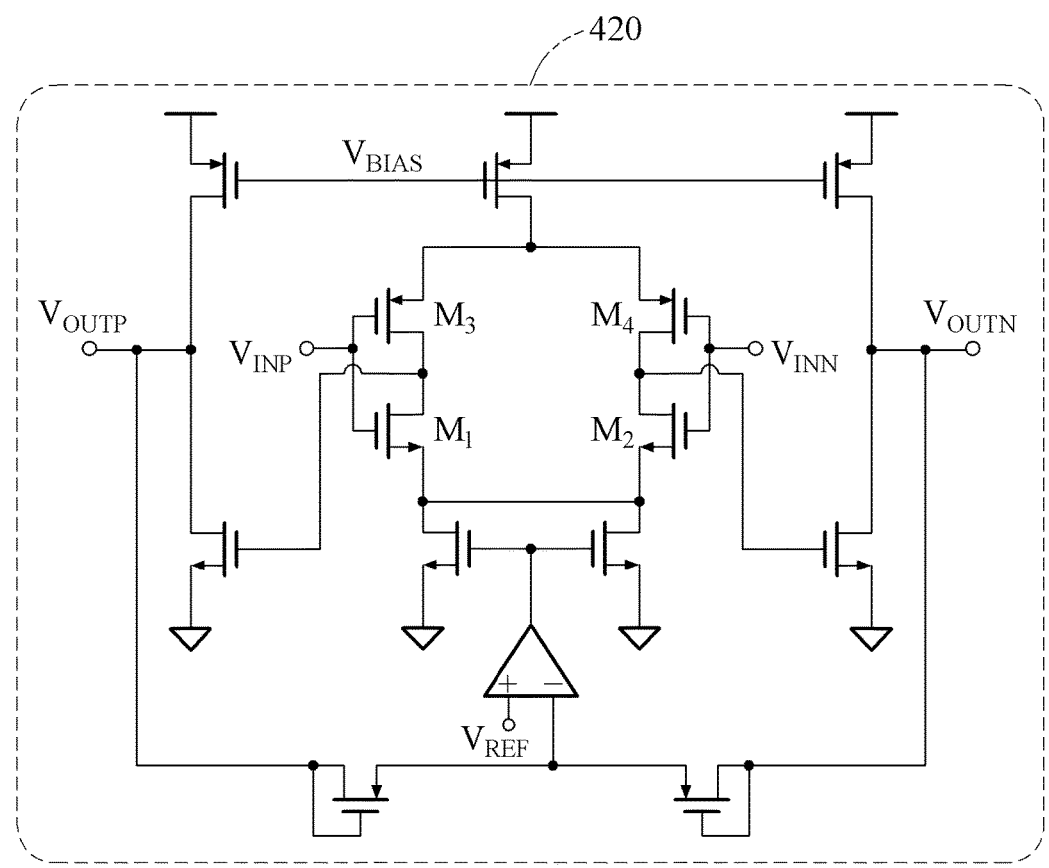

FIGS. 4A through 4C are diagrams illustrating an architecture and an LNA of a 16-channel neural recording amplifier system according to an embodiment. FIG. 4A illustrates an architecture of the proposed 16-channel neural amplifier system employing $DR^3E$. FIG. 4B illustrates an architecture of an LNA 410. FIG. 4C illustrates an architecture of an amplifier 420. A nested current recycling technique, where current is reused across stacked channels and also within an LNA (devices $M_1$-$M_4$), is used to strike an optimum of power, noise efficiency and gain. Rejection ratio enhancement is achieved using a frequency-controlled differential regulator (FCDR) that isolates the local rails ($V_{DD\_LNA}$, $V_{MID}$, and $V_{SS\_LNA}$) from the system rails, while making them closely track the $V_{CM}$ variations. FCDR uses a high-gain amplifier $G_{Amp}$ that superimposes the common-mode signal $V_{CM}$ derived from an additional electrode on the floating supply $V_{REG}$ through a unity-gain feedback network. $V_{REG}$ is derived from a supply- and ground-independent frequency reference $F_{OSC}$. Thus, the proposed $DR^3E$ may improve both CMRR as well as PSRR. Furthermore, the frequency reference from which $V_{REG}$ is derived may be used as a system clock for avoiding the use of a bulky crystal.

Figure 5A:
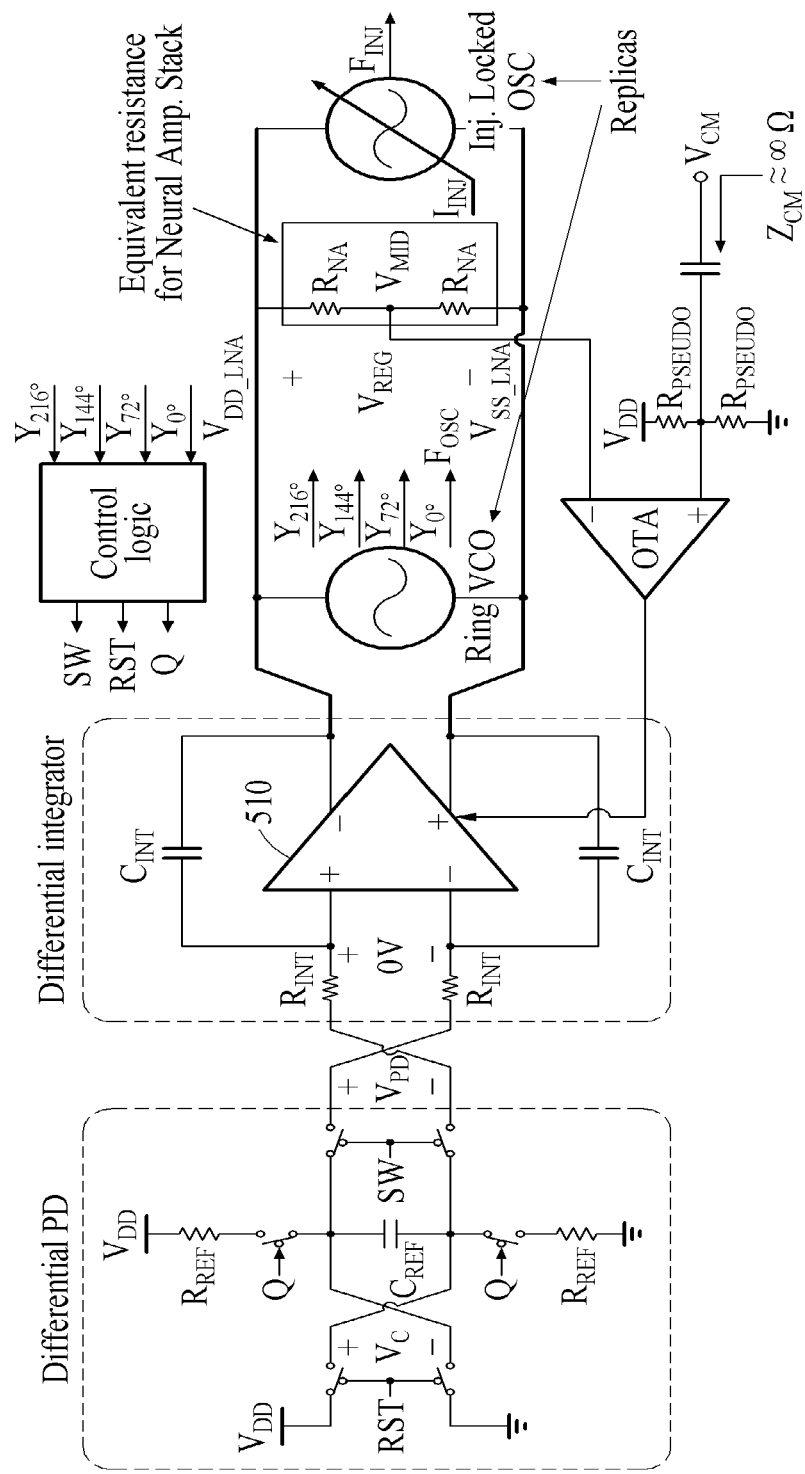
FIGS. 5A through 5C are diagrams illustrating timing waveforms of a frequency controlled differential regulator according to an example embodiment.
Figure 5B:
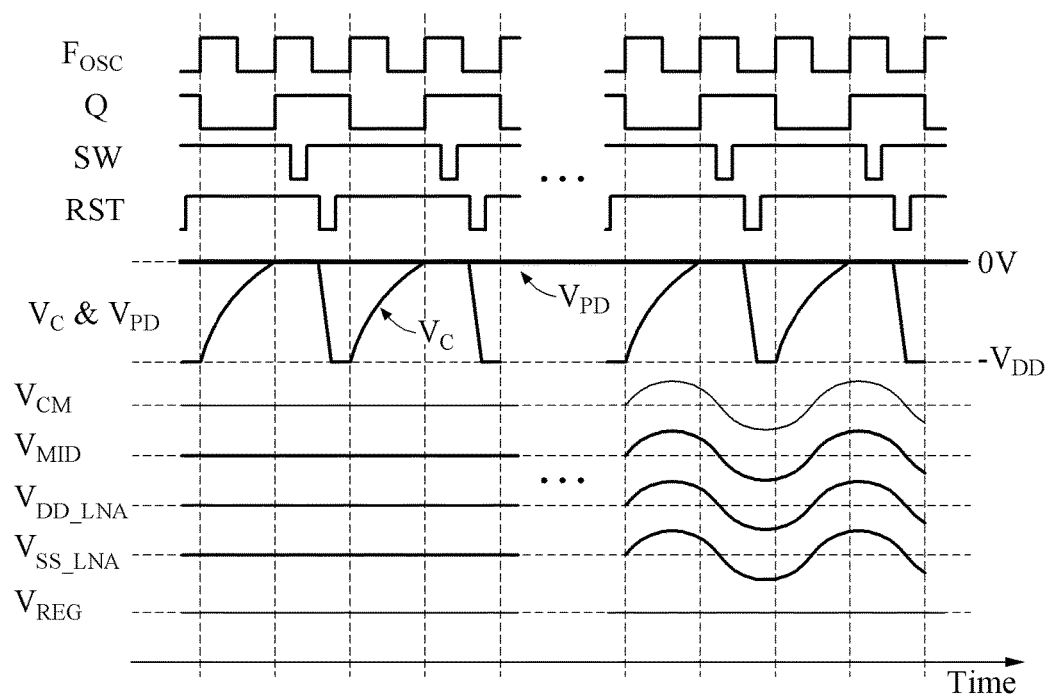
Figure 5C:
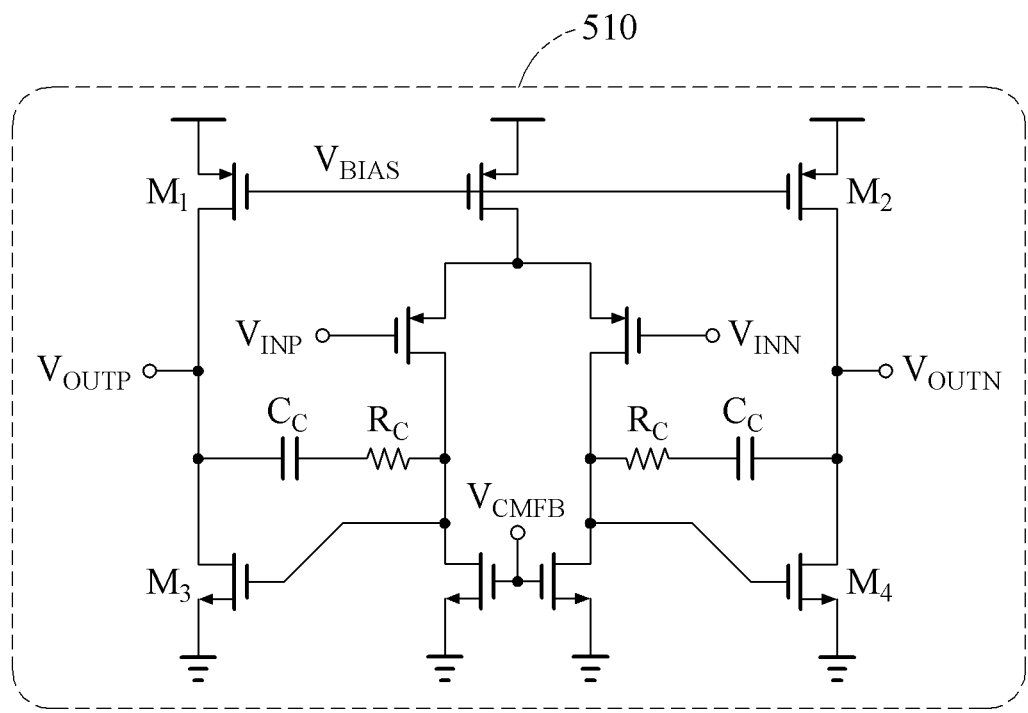

FIGS. 5A through 5C are diagrams illustrating timing waveforms of a frequency controlled differential regulator according to an embodiment. FIG. 5C illustrates an architecture of an amplifier 510. FIGS. 5A through 5C show the implementation of the frequency controlled differential regulator (FCDR) that generates the local rail of the neural amplifier stack $V_{REG}$, which is also the control voltage of the ring VCO. Through the negative feedback loop formed by the differential PD and the differential integrator, the VCO is locked to a frequency proportional to the $1/R_{REF}C_{REF}$ making $V_{REG}$ independent of supply and ground variations, enhancing the overall PSRR. The integrator also delivers power to the neural amplifier stack via the transistors $M_1$-$M_4$. The common-mode level of the integrator is forced to track the $V_{CM}$ variations through the unity-gain feedback set by the OTA and the integrator.

As a result, refer to FIG. 5B, the local rails of the amplifier stack, $V_{DD\_LNA}$, $V_{MID}$, and $V_{SS\_LNA}$ also tracks $V_{CM}$, effectively superimposing $V_{CM}$ on $V_{REG}$, enhancing the CMRR. However, the impedance $Z_{CM}$ needs to be maximized to ensure that the $V_{CM}$ is detected accurately regardless of the electrode impedance $Z_e$. To achieve this, a high-value pseudo resistor $R_{PSEUDO}$ is used to set the gate bias of the OTA. The differential regulator also drives a replica VCO that may be injection locked to a low-phase-noise clock derived from the wireless power supply. This high quality clock output may be used for communication purposes at the system level.

Figure 6A:
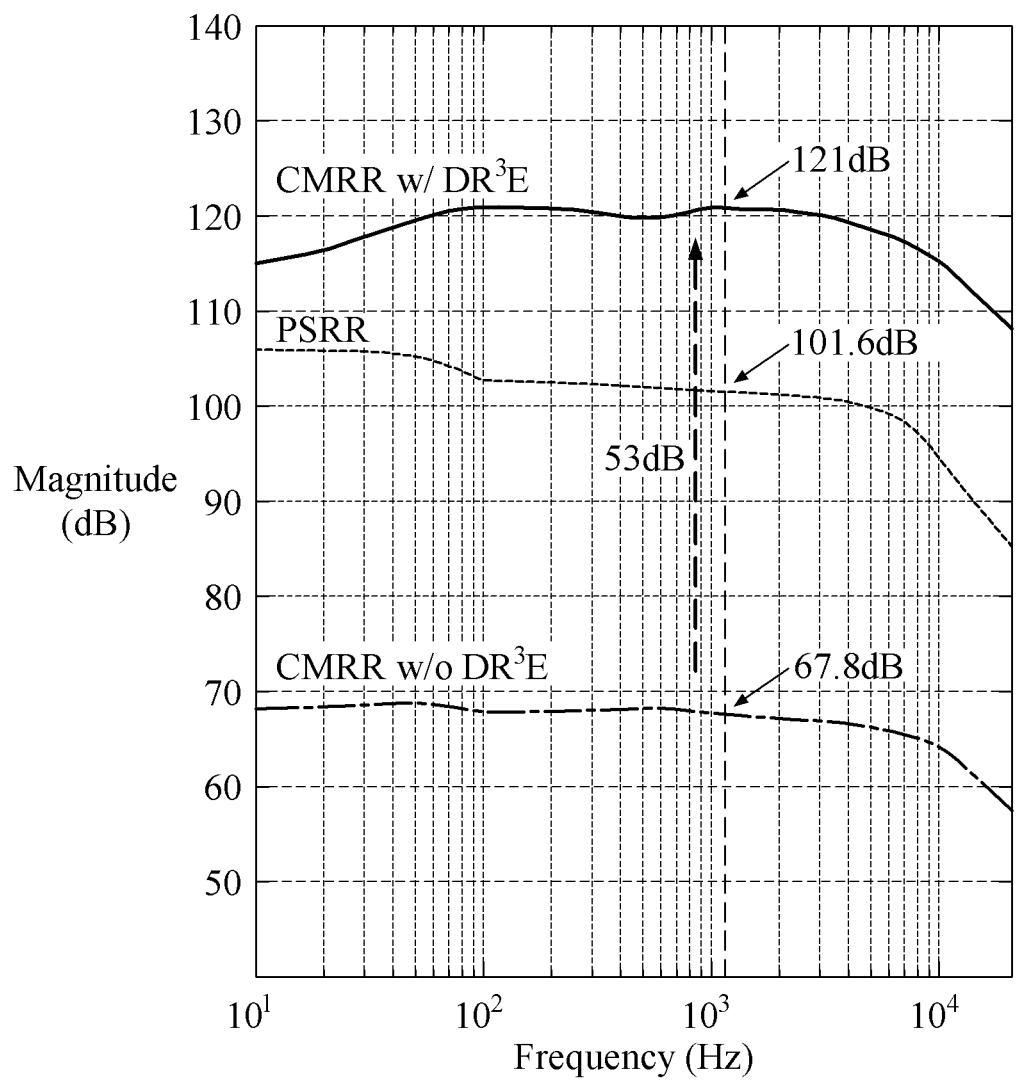
FIGS. 6A and 6B are diagrams illustrating a measured CMRR, PSRR and TCMRR across all 16 channels of one implementation of FIGS. 4A through 4C.
Figure 6B:
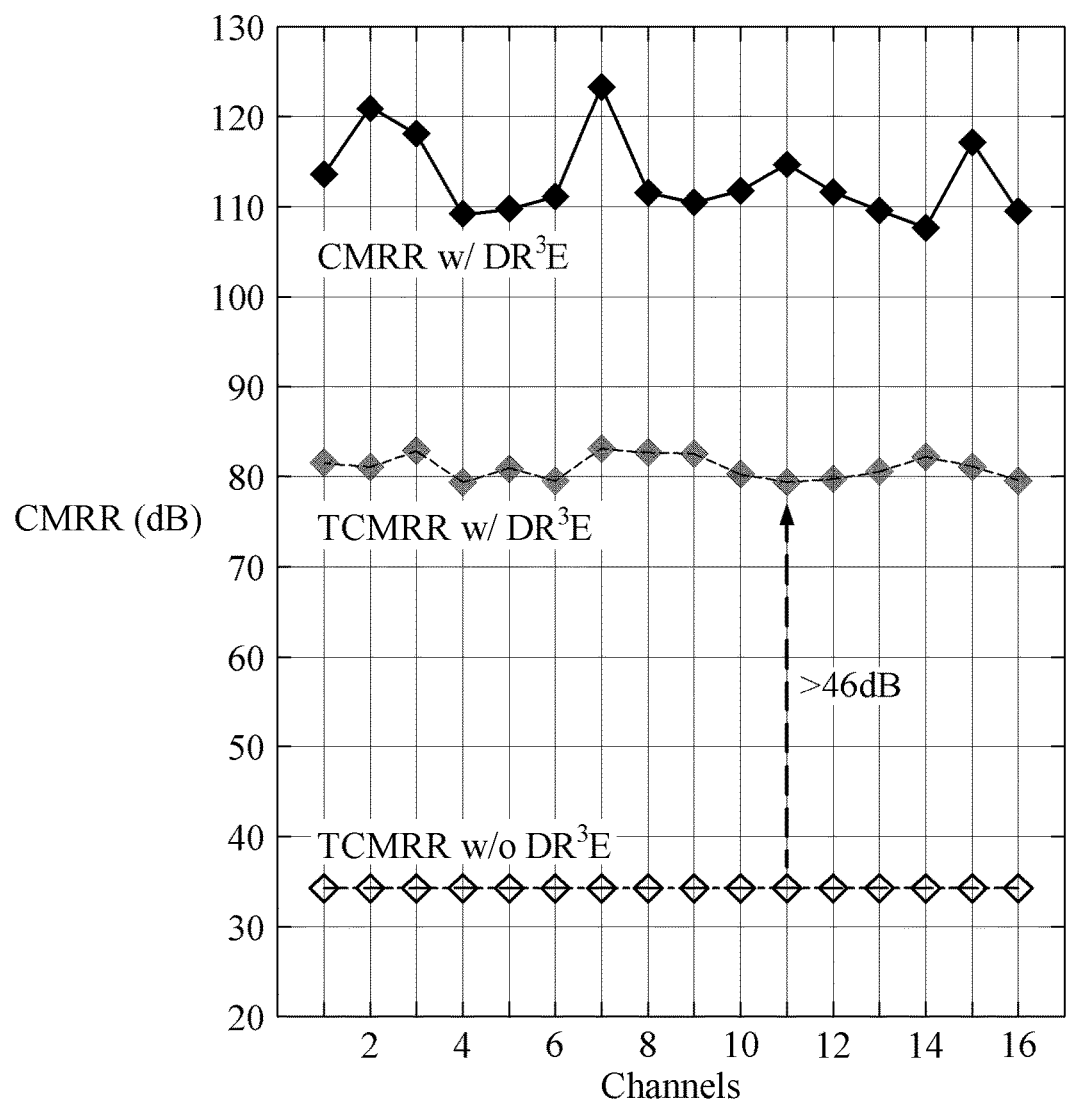

FIGS. 6A and 6B are diagrams illustrating a measured CMRR, PSRR, and TCMRR across all the 16 channels of one implementation of FIGS. 4A through 4C. In a 0.18 μm standard CMOS process, the neural amplifier system according to an embodiment occupies an active area of 2.3 mm² with an individual channel occupying 0.075 mm². From a 1.5V supply, the neural amplifier system consumes 51.7 μW of power while a single consumes 0.69 μW.

According to FIG. 6A, the $DR^3E$ technique helps to achieve a CMRR greater than 110 dB over a frequency range of 10 Hz-10 kHz. The PSRR is greater than 100 dB over a frequency range of 10 Hz-4 kHz and reaches 94 dB at 10 kHz. At 1 kHz, the CMRR is increased from 67.8 dB to 121 dB, which is a 53 dB improvement.

As shown in FIG. 6B, at 1 kHz, the worst-case CMRR across all channels is 110 dB, whereas the worst-case TCMRR at an electrode impedance of 100 kΩ is 80 dB. From 34 dB, this amounts to an improvement of more than 46 dB.

FIGS. 7A through 7D are diagrams illustrating a measured gain-bandwidth and input-referred noise of the LNA (7A and 7B), a supply variation of the FCDR output voltage $V_{REG}$ and the ring-VCO frequency $F_{OSC}$ (7C), phase-noise performances of the ring-VCO and injection-locked replica VCO (7D).

Figure 7A:
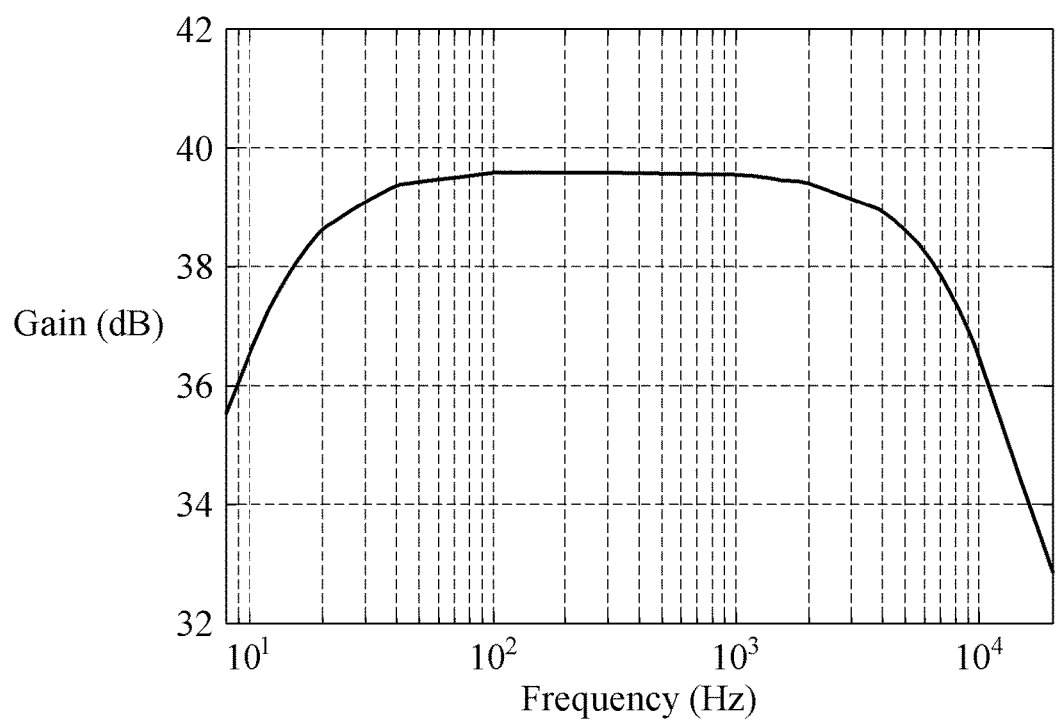
FIGS. 7A through 7D are diagrams illustrating a measured gain-bandwidth and input-referred noise of an LNA (7A and 7B), a supply variation of an FCDR output voltage $V_{REG}$ and a ring-VCO frequency $F_{OSC}$ (7C), and phase-noise performances of a ring-VCO and injection-locked replica VCO (7D)
Figure 7B:
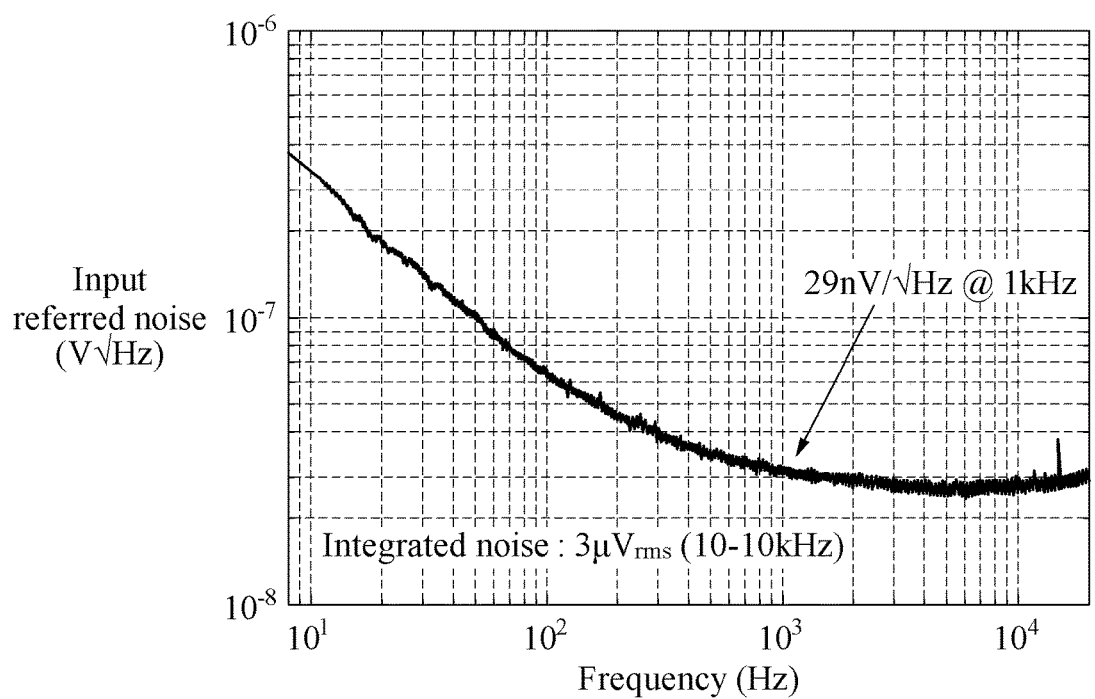
Figure 7C:
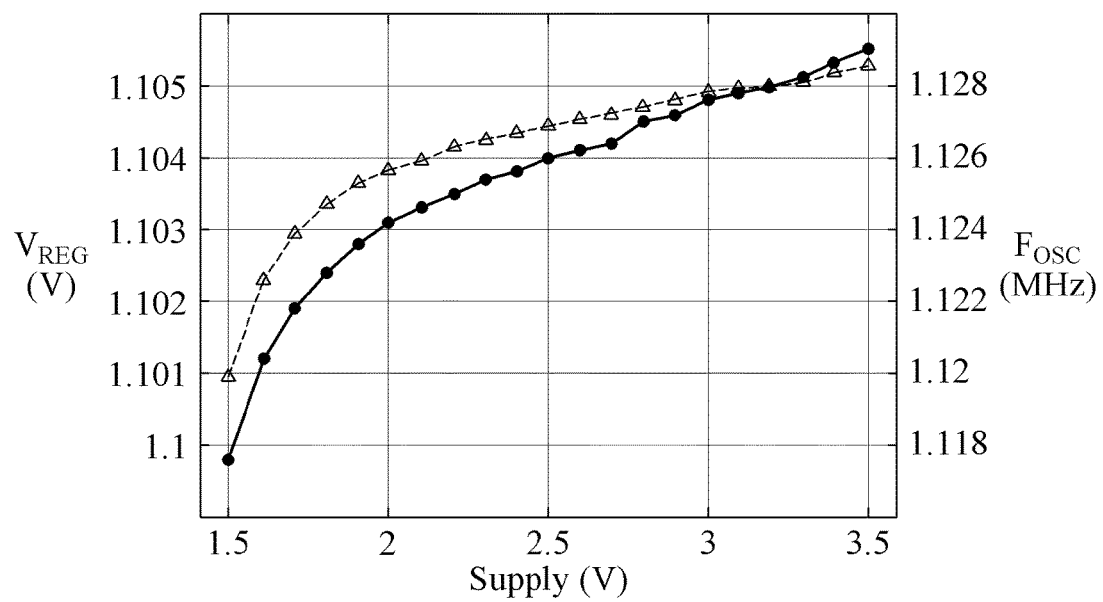
Figure 7D:
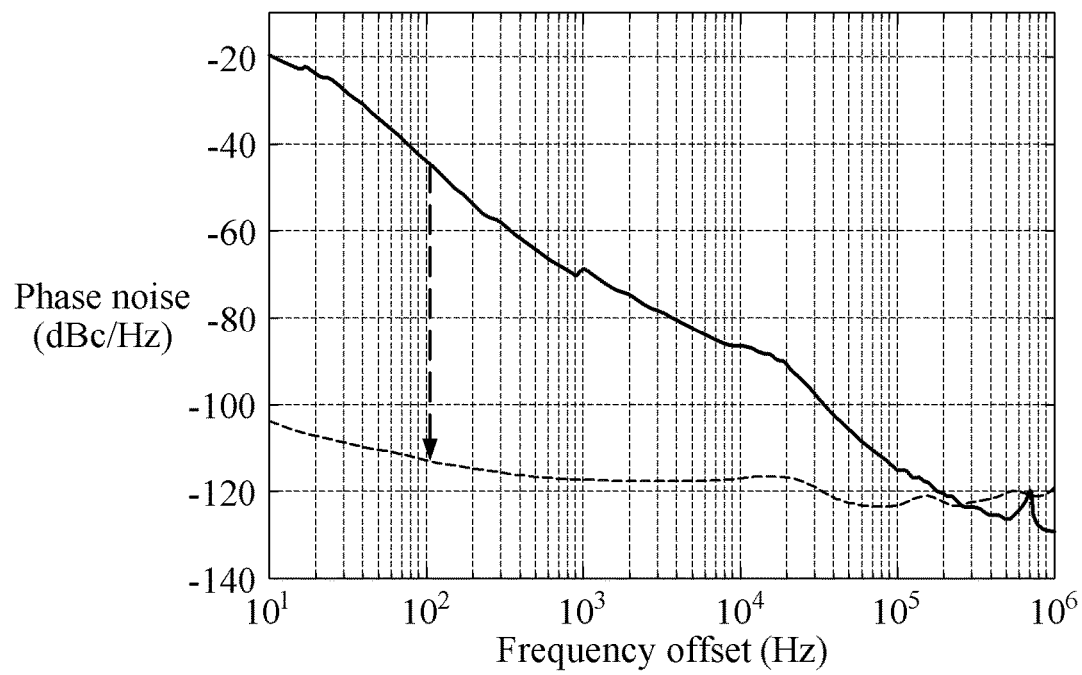

FIG. 7A shows that the neural amplifier flat band gain is 39.8 dB over a bandwidth of 10 Hz-10 kHz. As shown in FIG. 7B, the input referred noise PSD at 1 kHz is 29 nV/√Hz while integrated noise over a bandwidth of 10 Hz-10 kHz is 3 μVrms. FIG. 7C shows the effectiveness of the differential regulator in preserving $V_{REG}$ and hence the frequency in the presence of supply variation. Over a supply range between 1.5 and 3.5V, the $V_{REG}$ varies only by 5.7 mV which corresponds to 2580 ppm/V. Over the same supply range, the frequency varies between 1.12 MHz to 1.28 MHz equivalent to ±0.19%/V. FIG. 7D shows the phase-noise measurements of the ring-VCO and the injection locked replica VCO. Injection locking improves the close-in phase-noise of the replica VCO to be lower than −100 dBc/Hz. At an offset of 100 Hz, the improvement is more than 69 dB.

In-vivo measurements on the subthalamic nucleus of an anesthetized Sprague Dawley rat recorded successfully using the proposed $DR^3E$ neural amplifier is shown in FIG. 8. From the performance benchmark shown in FIG. 8, the CMRR of the $DR^3E$ neural amplifier is 30 dB better, while TCMRR is 20 dB better than the prior works. Similarly, the PSRR at 1 kHz is 20 dB better than those of the prior works. Other key performance figures such as NEF/PEF, input referred noise are better or comparable to those of the prior works.

The present invention provides a neural recording system that employs a differentially regulated rejection ratio enhancement scheme that improves the CMRR/TCMRR/PSRR performance by several tens of dBs over prior works, without the need for any bulky decoupling capacitors. Furthermore, the internal clock sources of the system may provide a high-quality clock for the system, obviating the need for bulky crystal oscillators. Thus, the proposed $DR^3E$ neural recording system paves a way for further miniaturization. Finally, though the proposed work is presented in the context of neural recording, it is also suitable for other biomedical signal acquisition applications where high CMRR/PSRR performance is essential.

The components described in the example embodiments of the present disclosure may be achieved by hardware components including at least one digital signal processor (DSP), a processor, a controller, an application specific integrated circuit (ASIC), a programmable logic element such as a field programmable gate array (FPGA), other electronic devices, and combinations thereof. At least some of the functions or the processes described in the example embodiments of the present disclosure may be achieved by software, and the software may be recorded on a recording medium. The components, the functions, and the processes described in the example embodiments of the present disclosure may be achieved by a combination of hardware and software.

The processing device described herein may be implemented using hardware components, software components, and/or a combination thereof. For example, the processing device and the component described herein may be implemented using one or more general-purpose or special purpose computers, such as, for example, a processor, a controller and an arithmetic logic unit (ALU), a digital signal processor, a microcomputer, a field programmable gate array (FPGA), a programmable logic unit (PLU), a microprocessor, or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will be appreciated that a processing device may include multiple processing elements and/or multiple types of processing elements. For example, a processing device may include multiple processors or a processor and a controller. In addition, different processing configurations are possible, such as parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums. The non-transitory computer readable recording medium may include any data storage device that can store data which can be thereafter read by a computer system or processing device. Examples of the non-transitory computer readable recording medium include read-only memory (ROM), random-access memory (RAM), CD-ROMs, magnetic tapes, floppy disks, optical data storage devices. Also, functional programs, codes, and code segments that accomplish the examples disclosed herein can be easily construed by programmers skilled in the art to which the examples pertain based on and using the flow diagrams and block diagrams of the figures and their corresponding descriptions as provided herein.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

The invention claimed is:

1. A differential voltage supplying apparatus, comprising:
a differential voltage generator configured to generate a first input signal and a second input signal from a power supply, wherein a difference between the first input signal and the second input signal is determined based on a preset potential difference; and
a common-mode signal combiner configured to combine a common-mode signal with each of the first input signal and the second input signal,
wherein the first input signal combined with the common-mode signal and the second input signal combined with the common-mode signal are inputted into a neural activity recorder having a plurality of detection electro nodes,
wherein the common-mode signal is determined based on a voltage applied to an electrode attached to a body of a user to allow the neural activity recorder to measure a neural activity of the user.

2. The differential voltage supplying apparatus of claim 1, wherein the common-mode signal combiner is configured to determine the common-mode signal using a common-mode signal electrode configured to measure a voltage applied to an electrode of the neural activity recorder.

3. The differential voltage supplying apparatus of claim 1, wherein the differential voltage generator is configured to generate the first input signal and the second input signal separated from the power supply and a ground electrode.

4. The differential voltage supplying apparatus of claim 1, wherein the common-mode signal combiner is configured to combine the common-mode signal with each of the first input signal and the second input signal to compensate for an influence of an impedance of a positive input terminal of a low-noise amplifier (LNA) included in the neural activity recorder and an impedance of a negative input terminal of the LNA, on a common-mode rejection ratio of the LNA.

* * * * *